(12) United States Patent
Schreiter et al.

(10) Patent No.: US 7,034,371 B2
(45) Date of Patent: Apr. 25, 2006

(54) BIOCHIP FOR THE CAPACITIVE STIMULATION AND/OR DETECTION OF BIOLOGICAL TISSUE AND A METHOD FOR ITS PRODUCTION

(75) Inventors: Matthias Schreiter, München (DE); Reinhard Gabl, München (DE); Martin Jenkner, Planegg (DE); Björn Eversmann, München (DE); Franz Hofmann, München (DE)

(73) Assignee: Infineon Technogies AG, Munich (DE)

( * ) Notice: Subject to any disclaimer, the term of this patent is extended or adjusted under 35 U.S.C. 154(b) by 153 days.

(21) Appl. No.: 10/701,113

(22) Filed: Nov. 3, 2003

(65) Prior Publication Data

US 2004/0119141 A1    Jun. 24, 2004

(30) Foreign Application Priority Data

Nov. 4, 2002   (DE)   ................ 102 51 243

(51) Int. Cl.
  *H01L 23/58* (2006.01)
  *H01L 27/14* (2006.01)
  *H01L 29/82* (2006.01)
  *H01L 29/84* (2006.01)
(52) U.S. Cl. .............. 257/414; 257/252; 257/253
(58) Field of Classification Search ........ 257/400, 257/252, 253, 288, 368, 414, 532, 535; 438/199, 438/957
See application file for complete search history.

(56) References Cited

U.S. PATENT DOCUMENTS

| | | | | |
|---|---|---|---|---|
| 5,674,366 A | * | 10/1997 | Hayashi et al. | 204/298.09 |
| 6,838,054 B1 | * | 1/2005 | Durrant | 422/82.02 |
| 2002/0076154 A1 | * | 6/2002 | Maisenhoelder et al. | 385/37 |
| 2002/0076561 A1 | * | 6/2002 | Vinet et al. | 428/446 |
| 2004/0023253 A1 | * | 2/2004 | Kunwar et al. | 435/6 |
| 2004/0046128 A1 | * | 3/2004 | Abel et al. | 250/458.1 |
| 2005/0043558 A1 | * | 2/2005 | Lebeau et al. | 558/17 |

FOREIGN PATENT DOCUMENTS

DE        196 23 517 C1    8/1997

* cited by examiner

*Primary Examiner*—Nathan J. Flynn
*Assistant Examiner*—Victor A. Mandala, Jr.
(74) *Attorney, Agent, or Firm*—Darby & Darby

(57) ABSTRACT

The present invention relates to a biochip for capacitive stimulation and/or detection of biological tissue. The biochip includes a support structure, at least one stimulation and/or sensor device, which is arranged in or on the support structure, and at least one dielectric layer, one layer surface of which is arranged on the stimulation and/or sensor device and the opposite layer surface forms a stimulation and/or sensor surface for the capacitive stimulation and/or detection of biological tissue. The dielectric layer includes $(Ti_x, Zr_{1-x})O_2$, with $0.99 \geq x \geq 0.5$, or a $TiO_2$ and $ZrO_2$ layer arrangement.

16 Claims, 3 Drawing Sheets

BIOCHIP FOR THE CAPACITIVE STIMULATION AND/OR DETECTION OF BIOLOGICAL TISSUE AND A METHOD FOR ITS PRODUCTION

CROSS-REFERENCE TO RELATED APPLICATIONS

This application claims priority to German Patent Application No. 102 51 243.4–52, filed Nov. 4, 2002, the entire disclosure of which is hereby incorporated by reference.

BACKGROUND OF THE INVENTION

1. Field of the Invention

The invention relates to a biochip for the capacitive stimulation and/or detection of biological tissue and to a method for producing such a biochip.

2. Description of the Related Art

Direct communication between nerve cells and electrically active solid-state structures, such as semiconductors for example, has already been a reality on a laboratory scale for a good decade. Successful laboratory trials were reported for example by P. Fromherz et al. in Science 252, 1290 (1991); P. Fromherz et al. in Physical Review Letters 75, 1670 (1995) and also P. Stett et al. in Physical Review E Vol. 55, No. 2, 1779 (1997). A summarizing overview of the early results is contained in P. Fromherz, Berichte der Bunsen Gesellschaft [Reports of the Bunsen Society] No. 7, 1093 (1996). More recently, first biochips produced on industrial scales have also been presented. Modern biochips consequently open up a wide variety of areas of use from basic neurobiological research through to high-throughput-screening applications in the pharmaceutical industry.

A basic element of modern biochips of this type is schematically represented in FIG. 1(a). The biochip comprises a support structure 10, which may comprise, for example, a patterned semiconductor substrate (semiconductor structure). The support structure 10 is separated from an electrolyte 14 by a dielectric layer 12. The corresponding equivalent circuit diagram is represented in FIG. 1(b). In general, the electrically communicating nerve cells are cultivated in an electrolyte directly at those locations on the surface of the support structure 10 at which the active locations of electrical stimulation and detection devices lie.

While in biological systems the electrical activity is carried by ions, in semiconductors electrons or holes are responsible for transporting the charge. Therefore, in a way corresponding to the natural boundary layer between the electrolyte 14 and the semiconductor structure, a capacitive coupling is preferably used both in the stimulation and in the detection of biological processes. This current-free mechanism of electrical coupling between the biochip and the nerve cell to be stimulated or to be detected is based on the principle of electrical induction (electrostatic induction). The electrical coupling is brought about by a charge accumulation in the nerve cell inducing corresponding mirror charges in the biochip, the influence of which, for example on the electrical transporting properties of the support structure 10 formed as a semiconductor structure, can be demonstrated.

Conversely, nerve cells which are arranged on the dielectric layer 12 of the support structure or semiconductor structure 10 can be stimulated by a charge accumulation in a stimulation device of the semiconductor structure 10 inducing charges in the nerve cell. In the case of a biochip of this type, which uses a capacitive coupling to the nerve cell to be investigated both in stimulation processes and in detection processes, the dielectric layer 12 between the semiconductor structure 10 and the electrolyte 14 takes on special significance.

Conventionally, silicone-based, active, and consequently CMOS-capable, semiconductor structures are coated with $SiO_2$, in order to form a dielectric boundary layer or surface layer 12 of this type. However, it has been found that a dielectric layer of $SiO_2$ produces only limitedly satisfactory results, in particular with regard to the coupling efficiency or the achievable signal transfer between the stimulation and/or sensor device of the biochip and the biological tissue to be investigated.

Most recently, $TiO_2$-based dielectric layers have found increasing interest for a large number of technical applications, for example as insulators in MOS structures, as moisture sensors or as passivation layers and protective coatings, on account of such properties as a high dielectric constant, high transparency, photocatalytic behavior and very good chemical resistance. In particular, the high dielectric constant of about 80 along with good passivation properties and good "biocompatibility", i.e. no substances with adverse effects on cell cultures are detached, make layers of this type of interest for the production of biochips. However, it has been established that $TiO_2$ layers on conductive electrodes, such as for example platinum, exhibit inadequate insulating properties, since the resistance already degrades under very low applied voltages. For example, high conductivities in thin $TiO_2$ (rutile) layers on conductive $RuO_2$ electrodes are also reported in B. H. Park et al., Applied Physics Letters, Vol. 80, No. 7, pages 1174–1176. Moreover, it is known that the conductivity of $TiO_2$ increases greatly even when there are extremely small deviations from the stoichiometric composition; cf. Gmelin Handbuch der anorganischen Chemie [Gmelin handbook of inorganic chemistry], published by Verlag Chemie, 1951, Titan [Titanium], page 251.

BRIEF SUMMARY OF THE INVENTION

The present invention is consequently based on the object of providing a biochip which is intended to permit improved coupling efficiency and/or increased signal transfer between stimulation and/or detection devices of the biochip and the biological tissue to be investigated, it being intended that the dielectric layer of such a biosensor should have improved insulating properties while at the same time retaining a relatively high dielectric constant. Furthermore, it is an object of the present invention to provide a method for producing a biochip of this type.

This object is achieved by the embodiments characterized in the claims.

In particular, a biochip for capacitive stimulation and/or detection of biological tissue is provided. The biochip includes a support structure, at least one stimulation and/or sensor device, which is arranged in or on the support structure, and at least one dielectric layer, one layer surface of which is arranged on the stimulation and/or sensor device and the opposite layer surface of which forms a stimulation and/or sensor surface for the capacitive stimulation and/or detection of biological tissue. The dielectric layer incldes $(Ti_x, Zr_{1-x})O_2$, with $0.99 \geq x \geq 0.5$, preferably $0.99 \geq x \geq 0.7$, and more preferably $0.99 \geq x \geq 0.85$, and/or a $TiO_2$ and $ZrO_2$ layer arrangement.

BRIEF DESCRIPTION OF THE DRAWINGS

The invention is described below by way of example with reference to accompanying drawings of preferred embodiments, in which.

DETAILED DESCRIPTION OF THE INVENTION

Figure 1:
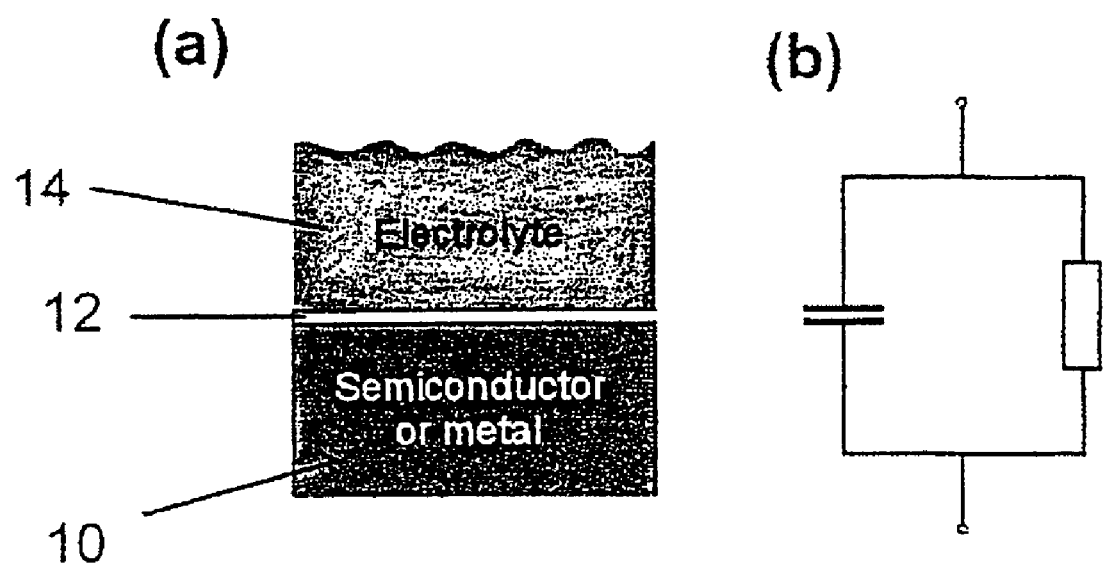
FIGS. 1(a) and (b) show a basic structure of the operational arrangement of a biochip in relation to an electrolyte with the associated equivalent circuit diagram.

According to the invention, the dielectric layer, which is operationally arranged between the support structure of the biochip and an electrolyte with the biological material to be investigated, comprises a Ti/Zr mixed oxide, i.e. $(Ti_x, Zr_{1-x})O_2$, with $0.99 \geq x \geq 0.5$, and/or a $TiO_2$ and $ZrO_2$ layer arrangement ("$TiO_2$ and $ZrO_2$ stack"). In particular such an arrangement of $TiO_2$ and $ZrO_2$ layers that are stacked alternately one on top of the other with a total number of (2n+1) layers ($n \geq 1$), the outer layers within the $TiO_2$ and $ZrO_2$ layer arrangement preferably being $TiO_2$ layers.

The support structure may be produced from a support substrate, for example by planar-lithographic process steps, as are known in particular from CMOS semiconductor technology. The stimulation and/or sensor device is preferably formed by a CMOS process in a silicon semiconductor substrate.

It has surprisingly been found that a $TiO_2/ZrO_2$-based dielectric layer, both a mixed oxide and a layer arrangement, has major advantages in comparison with conventional dielectric boundary layers of $SiO_2$ or $TiO_2$. In particular, a $TiO_2/ZrO_2$-based dielectric layer leads to a distinctly improved coupling efficiency or to a higher signal transfer between the biochip and the biological material in comparison with a $SiO_2$ boundary layer. In comparison with a dielectric layer just of $TiO_2$, the modification with $ZrO_2$, as a mixed oxide or by means of inducing one or more intermediate $ZrO_2$ layers to form a "$TiO_2$ and $ZrO_2$ stack", brings about a distinctly improved insulating property of such a dielectric layer, with a relatively high dielectric constant being retained at the same time.

The following advantages of a biochip according to the invention with a $TiO_2/ZrO_2$-based dielectric boundary layer are emphasized in particular:

(a) High Specific Capacitance

On the basis of the relationship $$c = \frac{\varepsilon_r \varepsilon_0}{d},$$

where c is the specific capacitance of the "boundary layer capacitor" in $F/m^2$, $\varepsilon_0 = 8.85 \times 10^{-12}$ As/Vm is the electric field constant, $\varepsilon_r$ is the relative dielectric constant and d is the thickness of the dielectric layer in meters, for a high specific capacitance the layer should on the one hand be as thin as possible and on the other hand consist of a material which has a great dielectric constant. The entire layer should also still have such a high dielectric constant when there are small layer thicknesses and when it is in contact with different materials.

It has been possible experimentally to achieve dielectric constants in the range of approximately 20 to 50 with biochips according to the invention which have $TiO_2/ZrO_2$-based dielectric boundary layers. Such dielectric constants lie distinctly above those of $SiO_2$, $Si_3Ni_4$, $Al_2O_3$, $ZrO_2$, $HfO_2$, $La_2O_3$, $Ta_2O_5$ and $Y_2O_3$. $ZrO_2$ in itself has a relatively low dielectric constant, that is about 12.

Since the specific capacitance of the support structure/electrolyte interface, which is dominated by the dielectric coating of the support structure, for example a semiconductor structure, is a major parameter in the optimization of the coupling efficiency or the signal transfer, a significant improvement over conventionally used dielectric boundary layers can be achieved by the specific choice of a combination of $TiO_2/ZrO_2$, whether as a mixed oxide $(Ti_x, Zr_{1-x})O_2$ or as a $TiO_2$ and $ZrO_2$ layer arrangement.

(b) Leakage Conductivity

The dielectric boundary layer of a biochip according to the invention has a very low leakage conductivity, so that electrolytic reactions on the surface of the layer which are accompanied by ohmic currents are ruled out.

In comparison with a dielectric layer just of $TiO_2$, the modification with $ZrO_2$, either as a $(Ti_x, Zr_{1-x})O_2$ mixed oxide or by means of introduction of one or more intermediate $ZrO_2$ layers to form a "$TiO_2$ and $ZrO_2$ stack", brings about a significantly lower leakage conductivity.

(c) Stability and Corrosion

In contrast with conventional capacitors, which are bounded at both ends by a solid-body contact, the "capacitor construction" of a biochip must withstand being contacted on one side by an aqueous solution with dissolved ions. In particular, the properties of the dielectric boundary layer are not to change even when an electrical voltage is applied. Furthermore, metabolic products of the biological material, for example of a cell culture, should not lead to chemical corrosion of the dielectric interface. It has surprisingly been established that—by contrast with $Si_3N_4$ layers for example—$TiO_2/ZrO_2$-based dielectric boundary layers have a high stability and low corrosion tendency.

(d) Biocompatibility

Conversely, the dielectric boundary layer must not release particles into the electrolyte, in particular under electrical voltage, either by dissolving or by corrosion. Since the interactions between the dielectric boundary layer and the biological tissue are of a complex nature, ultimately only the vitality of cells on the surface of the layer is a measure of the biocompatibility of the applied biological material. Vitality is to be understood in particular as meaning the retention of growth capability, which permits the formation of neurites on the surface.

Surprisingly, a $TiO_2/ZrO_2$-based dielectric layer, whether as a $(Ti_x, Zr_{1-x})O_2$ mixed oxide layer or as a $TiO_2$ and $ZrO_2$ layer arrangement, satisfies this requirement in an outstanding way. It has thus been possible successfully to demonstrate growth of cell structures on layers. $TiO_2/ZrO_2$-based dielectric layers are consequently superior to surface coatings which contain poisonous heavy metals or other toxic substances (such as for example PZT, which contains lead).

(e) Surface Finish

It has been found that a $TiO_2/ZrO_2$-based dielectric layer has, furthermore, a particularly advantageous surface finish. The capability of growing cells is consequently dependent not only on the composition of the boundary layer but also in particular on the topology of the surface on which the cells are cultivated. The surface preferably has an only slightly pronounced topology. In particular, the characteristic variables of the surface structure should lie in ranges several orders of magnitude below those which are used for example to cause targeted cell growth. For typical cells, the surface structures should consequently be smaller than 10 nm. Such planar surfaces additionally keep open the possibility of micromechanical or photolithographic patterning.

These properties are satisfied in an outstanding way by a $TiO_2/ZrO_2$-based dielectric layer used according to the invention. Furthermore, it has been possible to establish that the growth of a cell culture has no appreciable effect on the surface structure of a dielectric layer of this type. Both before and after the growth of the cell structure, the variations in the height of the dielectric surface were only a few nanometers, so that the boundary surface can be classified as smooth.

(f) Cleanability

It has been found that smooth $TiO_2/ZrO_2$-based dielectric layers of this type additionally offer the advantage of easy cleanability. Surfaces for the growth of cell cultures should preferably not only be smooth but also completely accessible for cleaning solutions and easily able to be rinsed. The dielectric layer of a biochip according to the invention is resistant in a wide pH range, so that customary cleaning solutions for biological materials, some of which have extreme pH values, can be used.

The cleanability of surfaces also includes their sterilizability. In the case of planar systems, UV sterilization is suitable in particular, but presupposes corresponding UV stability. The UV stability of $TiO_2/ZrO_2$-based dielectric layers is advantageously so pronounced that biochips according to the invention can be subjected to sterilization treatment by UV irradiation before being operationally used. The UV resistance of such $TiO_2/ZrO_2$-based layers consequently represents an important advantage over the usually organic surface coatings.

(g) Homogeneity

Furthermore, it has been possible to show that $TiO_2/ZrO_2$-based dielectric layers can be produced with adequate homogeneity. The previously described requirements for the dielectric layer should preferably be satisfied for the entire stimulation and/or sensor surface. Even small areas with high layer conductivity are sufficient for example to destroy the desired insulator character of the entire layer. A similar situation applies to a distribution of the dielectric constant or to the layer thickness.

(h) CMOS Integratability

One particular advantage of the $TiO_2/ZrO_2$-based dielectric boundary layers is the CMOS integratability. The position of the dielectric layer in the uppermost, and consequently last-processed, layer of a CMOS process means that the already existing structures have to be taken into consideration when it is deposited. This restricts in particular the temperature range of the depositing process used and also the duration of the process step. The process of depositing the dielectric layer must consequently fit into the "temperature budget" of the biochip in the back-end process stage. Preferably, a maximum temperature of approximately 500° C. should not be exceeded.

It has surprisingly been found that $TiO_2/ZrO_2$-based layers of a quality which satisfies all the above properties can be deposited for example by means of reactive RF sputtering at temperatures around 400° C. Such a reactive RF sputtering process can also be used as a back-end process in a CMOS production process. A sputtering process with pulsed DC sources can also be used.

The $TiO_2/ZrO_2$-based dielectric boundary layers used according to the invention also have the advantage that their production does not adversely change in any other way the already processed structures underneath the surface layer. Furthermore, such $TiO_2/ZrO_2$-based dielectric boundary layers used according to the invention can be produced by industrially customary processes on semiconductor wafers of a customary size.

Within the scope of the present invention, the stimulation device preferably comprises a metal electrode, the electrical potential of which is externally controllable and the dielectric layer is arranged on the metal electrode.

The support structure preferably comprises a semiconductor structure. The semiconductor structure may be, in particular, a silicon CMOS structure.

The sensor device preferably comprises a field-effect transistor with a source contact, a drain contact and a gate contact. The field-effect transistor may be, in particular, a p-transistor or a n-transistor, which is formed in the "front-end" of a CMOS process.

The dielectric layer used according to the invention is preferably arranged on a metal electrode of the sensor device which is connected in an electrically conductive manner to the gate contact of the field-effect transistor. The semiconductor structure is preferably a CMOS semiconductor structure. In particular, the metal electrode may be connected in an electrically conductive manner to the gate contact via an arrangement of metal and intermetal layers of the CMOS semiconductor structure. While the field-effect transistor of the CMOS semiconductor structure was defined in the "front-end", the arrangement of the metal electrode and the $TiO_2/ZrO_2$-based dielectric boundary layer takes place in the "back-end", i.e. in a later stage of the process.

The sensor device of such a biochip accordingly has two series-connected capacitances, which influence the coupling efficiency. For instance, the sensor device has a junction capacitance which is defined by the electrolyte—$TiO_2/ZrO_2$-based dielectric boundary layer—metal electrode arrangement. In addition, the coupling efficiency is influenced by the gate capacitance of the MOSFET, which is determined by the metal or polysilicon—$SiO_2$ semiconductor arrangement. A good coupling efficiency between the biochip and the electrolyte is achieved when the junction capacitance is as high as possible.

In the case of an embodiment of a biochip according to the invention of a particularly simple construction, the $TiO_2/ZrO_2$-based dielectric boundary layer may represent the gate oxide of the field-effect transistor. Consequently, the gate oxide of the FET directly forms the dielectric boundary layer between the electrolyte and the semiconductor. The gate contact, which otherwise consists of metal or polysilicon, is in this case provided by the electrolyte. Such a construction may be advantageous on account of the simple way in which it can be produced as a "laboratory specimen biochip".

The dielectric layer, whether it is as a $(Ti_x, Zr_{1-x})O_2$ mixed oxide layer or as a $TiO_2$ and $ZrO_2$ layer arrangement, preferably has an overall layer thickness of between 5 nm and 200 nm. Within the $TiO_2$ and $ZrO_2$ layer arrangement, the one or more $ZrO_2$ layers can be formed as thinly as possible, in dependence on the dielectric constant aimed for, for example in a thickness of from 5 to 10 nm.

According to the invention, a method for producing a biochip, in particular a biochip according to the invention, for the capacitive stimulation and/or detection of biological tissue comprises the steps of providing a support structure, forming at least one stimulation and/or sensor device in or on the support structure, arranging a dielectric layer of $(Ti_x, Zr_{1-x})O_2$, with $0.99 \geq x \geq 0.5$, preferably $0.99 \geq x \geq 0.7$, and more preferably $0.99 \geq x \geq 0.85$, or a $TiO_2$ and $ZrO_2$ layer arrangement on the stimulation and/or sensor device in such a way that one layer surface of the dielectric layer is arranged on the stimulation and/or sensor device and the opposite layer surface of the layer forms a stimulation and/or sensor surface for the capacitive stimulation and/or detection of biological tissue.

The arranging of the dielectric layer is preferably performed by means of sputtering a metallic titanium target and a metallic zirconium target in an argon/oxygen mixture. If the dielectric layer is made up of a $(Ti_x, Zr_{1-x})O_2$ mixed oxide, the step of arranging the dielectric layer preferably comprises the simultaneous sputtering of $TiO_2$ and $ZrO_2$. In this case, the substrate to be coated (support material with stimulation and/or sensor device) is usually arranged on a turntable, a mixed oxide of a composition determined by the ratio of the generator outputs with which the titanium and zirconium targets are fed being deposited by the rotation of the turntable. If the dielectric layer is made up of a $TiO_2$ and $ZrO_2$ layer arrangement, the step of arranging the dielectric layer preferably comprises the sputtering of $TiO_2$ and $ZrO_2$ in such a way that $TiO_2$ and $ZrO_2$ layers are stacked alternately one on top of the other with a total number of (2n+1) layers ($n \geq 1$), $TiO_2$ layers preferably being deposited as the outer layers within the $TiO_2$ and $ZrO_2$ layer arrangement ("$TiO_2$ and $ZrO_2$ stack"). With layer-by-layer depositing, the substrate to be coated usually remains over the respective target in a way corresponding to the depositing rate and desired thickness.

The sputtering may be performed for example by means of RF sputtering or sputtering with a pulsed DC source. The arranging of the dielectric layer may also be performed at the end (i.e. in the "back-end") of a CMOS process.

Represented in FIG. 2(a) is an embodiment of a biochip according to the invention in a field-effect transistor configuration which is used as a potential sensor. The biochip has a patterned support structure 10, which is a semiconductor structure. The substrate of the semiconductor structure 10 is electrically contacted by means of an ohmic contact and electrically connected to a voltage source $V_{BS}$. Arranged in the semiconductor structure 10 is a source contact 16 and a drain contact 18 of a field-effect transistor, which are respectively electrically contacted.

Arranged in the gate region of the field-effect transistor, between the source contact 16 and the drain contact 18, is a $TiO_2/ZrO_2$-based dielectric layer 12, which separates the semiconductor structure 10 from the electrolyte or the bath 14. The dielectric layer 12 may in this case be made up of $(Ti_x, Zr_{1-x})O_2$, with $0.99 \geq x \geq 0.5$, or a $TiO_2$ and $ZrO_2$ layer arrangement, as explained above. The dielectric layer 12 consequently represents the gate oxide of the field-effect transistor.

Figure 2:
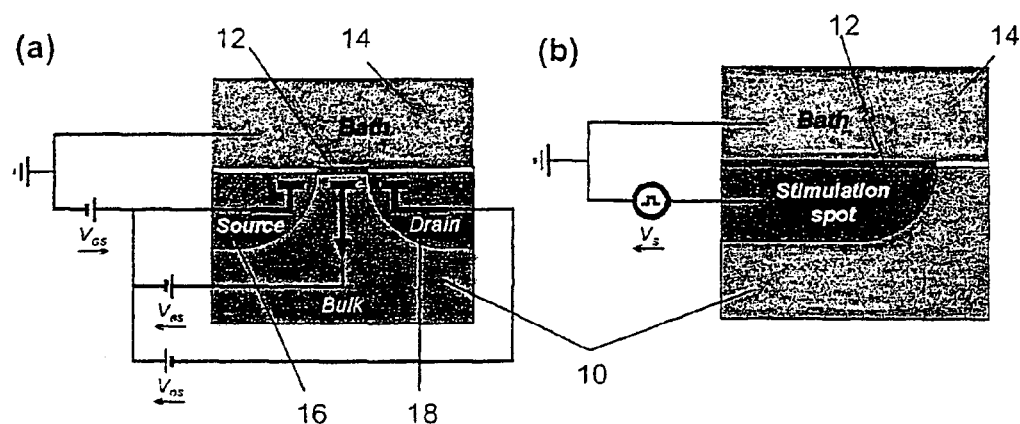
FIG. 2(a) shows an embodiment of a biochip according to the invention in a field-effect transistor configuration as a potential sensor.
FIG. 2(b) shows a further embodiment of a biochip according to the invention in a stimulation configuration.

Consequently, the embodiment represented in FIG. 2 is a "laboratory specimen biochip", which has a particularly simple construction. A CMOS-compatible biochip according to the invention has a much more complex construction of the semiconductor structure 10. In particular, in the case of a CMOS-compatible biochip, the gate oxide of the field-effect transistor (FET) is not formed by the $TiO_2/ZrO_2$-based dielectric boundary layer used according to the invention. Instead of this, the FET of a CMOS-compatible biochip has a conventional construction with a polysilicon gate contact and an $SiO_2$ gate oxide. The gate contact is in this case connected via an arrangement of metal and intermetal tracks to a metal electrode near the surface, which bears the $TiO_2/ZrO_2$-based dielectric boundary layer 12. However, for reasons of easier understanding of the basic principle according to the invention, the further description is based on a "laboratory specimen biochip".

The surface of the dielectric layer 12 facing away from the semiconductor substrate 10, i.e. that interface which is operationally in contact with the electrolyte 14, represents a sensor surface for the capacitive detection of biological tissue or processes. In simple terms, in the case of a "laboratory specimen biochip" the conventionally metallic gate electrode of the field-effect transistor is replaced by the electrolyte. Charge transfers or changes in electrical potential in the biological material which is located near the dielectric layer 12 in the electrolyte 14 consequently change the electrical transporting properties of the field-effect transistor via the field effect. In particular, the electrical conductivity between the source contact 16 and the drain contact 18 is influenced by such changes in potential. This changing of the channel conductivity of the field-effect transistor can be demonstrated in the customary way. The dielectric layer 12 may also have a greater lateral extent than the channel region of the field-effect transistor.

Represented in FIG. 2(b) is an embodiment of a biochip according to the invention in a stimulation configuration. A stimulation device, which comprises, for example, a doped semiconductor region of the semiconductor structure 10 or a metal electrode, is electrically contacted, so that an external voltage signal can be applied in relation to the electrical potential of the electrolyte. Arranged between the stimulation device and the electrolyte 14 is a $TiO_2/ZrO_2$-based dielectric layer 12 used according to the invention. The interface of the dielectric layer 12 facing away from the stimulation device represents a stimulation surface for the capacitive stimulation of biological tissue. This capacitive stimulation surface, which is also referred to as a stimulation spot, allows the capacitive excitation of biological material to be investigated. The dielectric layer may also have a lateral extent beyond the stimulation device.

Figure 3:
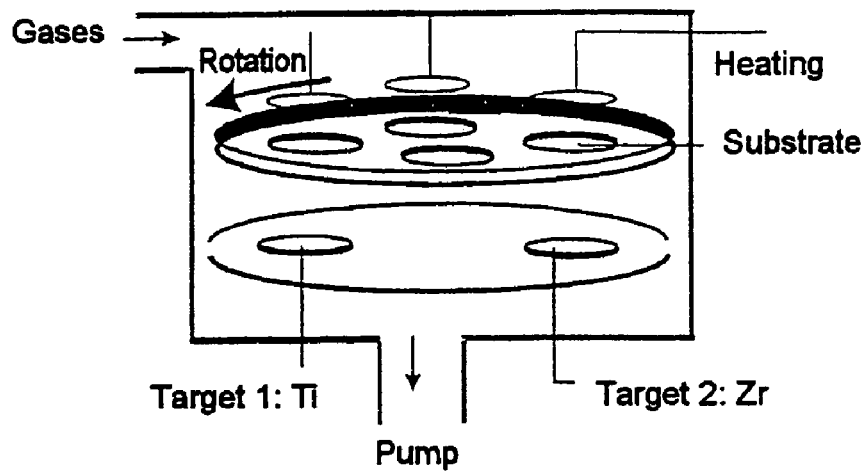
FIG. 3 shows a schematic representation of the sputtering process as part of the production of a biochip according to the invention.

Variants of the way in which the method of production according to the invention is implemented are specified below. The dielectric layer is applied on the stimulation and/or sensor device by means of a $TiO_2$ and $ZrO_2$ sputtering process. In this process, a $(Ti_x, Zr_{1-x})O_2$ mixed oxide or alternatively a $TiO_2$ and $ZrO_2$ layer arrangement is sputtered on from a metallic titanium target and a metallic zirconium target in an argon/oxygen mixture at 0.4 Pa and a distance of 60 mm. The atomized titanium or zirconium material reacts with the $O_2$ molecules in the gas space to form $TiO_2$ or ZrO$_2$. If a (Ti$_x$, Zr$_{1-x}$)O$_2$ mixed oxide is to be deposited, a mixed oxide of a composition which is determined by the ratio of the generator outputs with which the targets are fed is deposited by the rotation of the turntable on which the substrate to be coated is arranged, as shown in FIG. 3. With layer-by-layer depositing, the substrate remains over the respective target in a way corresponding to the depositing rate and desired thickness. An alternating sputtering of TiO$_2$ and ZrO$_2$ then takes place in such a way that TiO$_2$ and ZrO$_2$ layers are stacked alternately one on top of the other with a total number of (2n+1) layers (n≧1), TiO$_2$ layers being deposited as the outer layers within the TiO$_2$ and ZrO$_2$ layer arrangement ("TiO$_2$ and ZrO$_2$ stack"). As an alternative to an RF sputtering process, a sputtering process with a pulsed DC source, which has an equivalent DC output of 3 kW, may be used.

Figure 4:
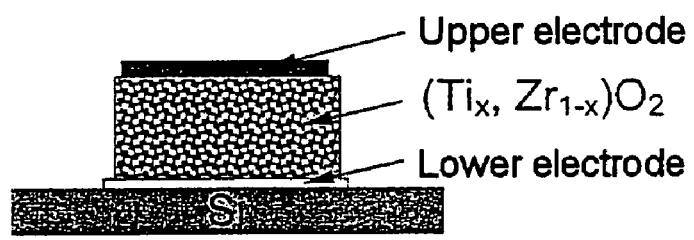
FIG. 4 shows a test setup of a thin-film capacitor with a $(Ti_x, Zr_{1-x})O_2$ dielectric layer, as used in a biochip according to the invention.
Figure 5:
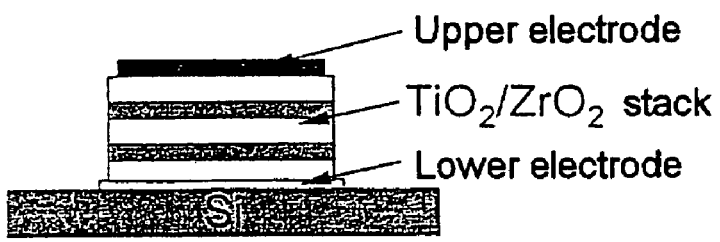
FIG. 5 shows a test setup of a thin-film capacitor with a $TiO_2$ and $ZrO_2$ layer arrangement, the $TiO_2$ and $ZrO_2$ layer arrangement being made up of $TiO_2$ and $ZrO_2$ layers which are stacked alternately one on top of the other with a total number of (2n+1) layers (n=2), the outer layers being $TiO_2$ layers, as used in a biochip according to the invention.

FIGS. 4 and 5 respectively show test setups of thin-film capacitors with a (Ti$_x$, Zr$_{1-x}$)O$_2$ dielectric layer (FIG. 4) and a TiO$_2$ and ZrO$_2$ layer arrangement, as can respectively be used in the biochip according to the invention. In the test setup according to FIG. 4, a (Ti$_x$, Zr$_{1-x}$)O$_2$ dielectric layer with a Zr component of 25% (x=0.75) has been deposited on Si—Al$_2$O$_3$—Pt with a layer thickness of about 35 nm. The substrate (wafer), heated to approximately 400° C., rotated under the targets, as schematically represented in FIG. 3, so that TiO$_2$/ZrO$_2$ was applied at an average rate of 2 nm/min. The dielectric layer obtained exhibited a dielectric constant of greater than 20. For this test setup, a leakage current density at 3 V of about 2.50 nA/mm$^2$ was determined. The value determined corresponds to less than $\frac{1}{10^4}$ of the leakage current density of a reference arrangement with a 50 nm thick TiO$_2$ layer as the dielectric on the same substrate.

In the test setup according to FIG. 5, a TiO$_2$ and ZrO$_2$ layer arrangement was deposited as the dielectric on Si—Al$_2$O$_3$—Pt with a layer thickness of about 50 nm. The stacked dielectric layer obtained exhibited a dielectric constant of about 50. For this test setup, a leakage current density at 3 V of about 15 pA/mm$^2$ was determined. The value determined corresponds to less than $\frac{1}{10^6}$ of the leakage current density of a reference arrangement with a 50 nm thick TiO$_2$ layer as the dielectric on the same substrate.

It has been found that such TiO$_2$/ZrO$_2$-based dielectric layers used according to the invention withstand a 10-minute bath at 80° C. under the influence of ultrasound in a cleaning solution which is sold under the brand name "Ticopur" without any ascertainable impairment of the interfacial properties. In this case, less than 1 nm of the surface layer of the dielectric layer is removed.

For testing the corrosion resistance, the biochips obtained were arranged in plastic petri dishes often used for neurobiological purposes ("Falcon 3001" type) and sterilized from both sides, for 30 minutes on each side, by UV irradiation in flow boxes.

The coating was performed with 2 ml of PBS (phosphate buffer saline) and 40 μl of collagen per dish, which after being applied by a pipette was left to act over night. On the following day, the Falcon dishes were rinsed once with ultrahigh-purity water (millipore) and filled with a nutrient medium (13.89 g of DMEM, 3.7 g of NaHCO$_3$, 1 l of water with a pH of 6.8 (HCl or NaOH)). The medium was sterile-filtered and mixed with 500 μl of L-glutamine, 5.5 ml of penicillin/streptomycin (antibiotics) and 100 ml of FCS (fetal calf serum).

The HEK cells cultivated in "Falcon 3001" petri dishes were removed by pipette from a dish, applied dropwise in a ratio of 1:4 to the biochips in the nutrient medium and left in an incubating cabinet under 37° C. and 5% CO$_2$. After 24, 36 and 72 hours, microscope pictures were taken to check the state of the cells and of the biochip.

All the cells exhibited a similar cell division rate, irrespective of the substrate, and showed no effects of being influenced in comparison with dielectric layers of SiO$_2$. It can be concluded from this that, in the case of all the materials investigated, on the one hand no substances which have adverse effects on the cell culture are detached, and on the other hand the morphology of the interfacial surface is in principle suitable for cell cultures.

What is claimed is:

1. A biochip for capacitive stimulation and/or detection of biological tissue comprising:
   a support structure;
   at least one stimulation and/or sensor device arranged in or on the support structure; and
   at least one dielectric layer, one layer surface of which is arranged on the stimulation and/or sensor device and the opposite layer surface of which forms a stimulation and/or sensor surface for the capacitive stimulation and/or detection of biological tissue;
   wherein the dielectric layer includes (Ti$_x$, Zr$_{1-x}$)O$_2$, with 0.99≧x≧0.5, or a TiO$_2$ and ZrO$_2$ layer arrangement.

2. The biochip as claimed in claim 1, wherein the TiO$_2$ and ZrO$_2$ layer arrangement includes TiO$_2$ and ZrO$_2$ layers stacked alternately one on top of the other with a total number of (2n+1) layers (n≧1), the outer layers being TiO$_2$ layers.

3. The biochip as claimed in claim 1, wherein the stimulation device includes a metal electrode, the electric potential of which is externally controllable, and wherein the dielectric layer is arranged on the metal electrode.

4. The biochip as claimed in claim 1, wherein the support structure includes a semiconductor structure.

5. The biochip as claimed in claim 4, wherein the sensor device includes a field-effect transistor with a source contact, a drain contact, and a gate contact.

6. The biochip as claimed in claim 5, wherein the dielectric layer is arranged on a metal electrode of the sensor device which is connected in an electrically conductive manner to the gate contact of the field-effect transistor.

7. The biochip as claimed in claim 4, wherein the semiconductor structure is a CMOS semiconductor structure.

8. The biochip as claimed in claim 6, wherein the metal electrode is connected in an electrically conductive manner to the gate contact via an arrangement of metal and intermetal layers of the CMOS semiconductor structure.

9. The biochip as claimed in claim 4, wherein the dielectric layer forms the gate oxide of a field-effect transistor.

10. The biochip as claimed in claim 1, wherein the dielectric layer has an overall layer thickness of between 5 nm and 200 nm.

11. A method for producing a biochip for capacitive stimulation and/or detection of biological tissue, comprising the steps of:
    providing a support structure;
    forming at least one stimulation and/or sensor device in or on the support structure; and
    arranging a dielectric layer of (Ti$_x$, Zr$_{1-x}$)O$_2$, with 0.99≧x≧0.5 or a TiO$_2$ and ZrO$_2$ layer arrangement on the stimulation and/or sensor device in such a way that one layer surface of the dielectric layer is arranged on the stimulation and/or sensor device and the opposite layer surface of the layer forms a stimulation and/or sensor surface for the capacitive stimulation and/or detection of biological tissue.

12. The method as claimed in claim 11, wherein the arranging of the dielectric layer is performed by sputtering a metallic titanium target and a metallic zirconium target in an argon/oxygen mixture.

13. The method as claimed in claim 11, wherein the step of arranging the dielectric layer includes the simultaneous sputtering of $TiO_2$ and $ZrO_2$, the substrate to be coated being arranged on a turntable in such a way that a $(Ti_x, Zr_{1-x})O_2$ mixed oxide of a composition determined by the ratio of the generator outputs with which the titanium and zirconium targets are fed being deposited by the rotation of the turntable.

14. The method as claimed in claim 11, wherein the step of arranging the dielectric layer includes the sputtering of $TiO_2$ and $ZrO_2$ in such a way that $TiO_2$ and $ZrO_2$ layers are stacked alternately one on top of the other with a total number of (2n+1) layers (n≧1), $TiO_2$ layers being deposited as the outer layers within the $TiO_2$ and $ZrO_2$ layer arrangement.

15. The method as claimed in claim 11, wherein the step of arranging the dielectric layer includes RF sputtering or sputtering with a pulsed DC source.

16. The method as claimed in claim 11, wherein the step of arranging the dielectric layer is performed as a back-end process step of a CMOS process.

* * * * *